United States Patent [19]

Newsome et al.

[11] Patent Number: 4,602,041
[45] Date of Patent: Jul. 22, 1986

[54] BENZYLIDENEAMINO- AND PHENYLACETYLGUANIDINES AND THEIR PHARMACEUTICAL USES

[75] Inventors: Peter M. Newsome, Cheam; Lee J. Beeley, Dorking; Stephen F. Moss, Carshalton, all of England

[73] Assignee: Beecham Group P.L.C., England

[21] Appl. No.: 464,978

[22] Filed: Feb. 8, 1983

[30] Foreign Application Priority Data

Feb. 10, 1982 [GB] United Kingdom ............... 8203916

[51] Int. Cl.$^4$ .................. A61K 31/155; C07C 129/12; C07C 133/10
[52] U.S. Cl. ..................................... 514/634; 514/400; 564/163; 564/237; 548/350; 548/351; 548/353
[58] Field of Search ............... 564/182, 163, 237, 165, 564/234; 424/324, 326; 548/350-351, 353; 514/400, 634; 260/501.14

[56] References Cited

U.S. PATENT DOCUMENTS

| | | | |
|---|---|---|---|
| 2,734,904 | 2/1956 | Burtner | 564/182 |
| 3,174,978 | 3/1965 | Marxer | 260/501.14 |
| 3,320,229 | 5/1967 | Szabo et al. | 564/237 |
| 3,349,099 | 10/1967 | Marxer | 564/234 |
| 3,560,557 | 2/1971 | Marxer | 260/501.14 |
| 3,634,508 | 1/1972 | Bream et al. | 564/182 |
| 4,018,814 | 4/1977 | Wallweber et al. | 564/182 |
| 4,332,814 | 6/1982 | Newsome et al. | 424/273 R |
| 4,450,170 | 5/1984 | Beeley et al. | 424/273 R |

FOREIGN PATENT DOCUMENTS 1223491 2/1971 United Kingdom .

*Primary Examiner*—Natalie Trousof
*Assistant Examiner*—L. Hendriksen
*Attorney, Agent, or Firm*—Jacobs & Jacobs

[57] ABSTRACT

Compounds of formula (I):

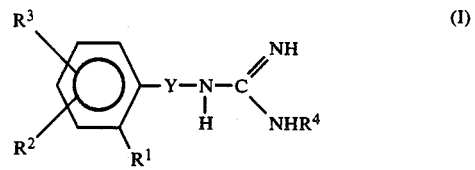

or a salt or acyl derivative thereof;
wherein
 Y is either —CH=N or

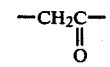

$R^1$ is hydroxy, halogen, $(C_{1-4})$ alkyl, or $(C_{1-4})$alkoxy,
$R^2$ is a nitrogen-containing, basic substituent,
$R^3$ is hydrogen, hydroxy, halogen, $(C_{1-4})$ alkyl, $(C_{1-4})$ alkoxy or a nitrogen-containing, basic substituent, and
$R^4$ is hydrogen or hydroxy,
are useful in treating diarrhoea and scours.

15 Claims, No Drawings

BENZYLIDENEAMINO- AND PHENYLACETYLGUANIDINES AND THEIR PHARMACEUTICAL USES

The present invention relates to novel guanidine derivatives, to processes for their production and to their use in medicine. The invention also relates to novel intermediates and to processes for their production.

Accordingly, the present invention provides a compound of formula (I):

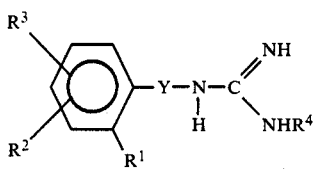

or a salt or acyl derivative thereof;
wherein
Y is either —CH=N— or

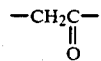

$R^1$ is hydroxy, halogen, $(C_{1-4})$ alkyl, or $(C_{1-4})$ alkoxy,
$R^2$ is a nitrogen-containing, basic substituent,
$R^3$ is hydrogen, hydroxy, halogen, $(C_{1-4})$ alkyl, $(C_{1-4})$ alkoxy or a nitrogen-containing, basic substituent, and,
$R^4$ is hydrogen or hydroxy.

As used herein the term "nitrogen-containing, basic substituent" refers to substituents comprising a nitrogen atom bonded directly to the phenyl ring in formula (I) or bonded via a single methylene group to that ring. Nitro substituents and similar neutral or acidic groups are not encompassed within this term. Particularly suitable nitrogen-containing, basic substituents include amino-, mono- or di-$(C_{1-4})$ alkylamino; aminomethyl; mono- or di-$(C_{1-4})$ alkylaminomethyl; amidino; guanidino and 2-imidazolino, the latter two being optionally substituted on a nitrogen atom, by $(C_{1-4})$ alkyl or acyl groups.

Suitable acyl substituents include the residues of optionally halogen substituted $(C_{1-4})$ alkanoic acids and of optionally substituted benzoic acid. Any substituents on the benzoic acid are, suitably, hydroxy, halogen, $(C_{1-4})$ alkyl, $(C_{1-4})$ alkoxy and amino groups.

Preferably $R^1$ is halogen, especially chlorine, or methyl.

Preferably $R^2$ is amino or dimethylamino. Most preferably $R^2$ is in the meta position with respect to the group Y in formula (I).

Preferably $R^3$ is halogen, especially chlorine, or methyl. Most preferably $R^3$ is situated in the ortho position with respect to the group Y in formula (I), and is the same as $R^1$.

Preferably $R^4$ is hydrogen.

Suitable salts include pharmaceutically or veterinarily acceptable salts, but it is not essential that salts are pharmaceutically or veterinarily acceptable as such salts may also be useful in producing or purifying the desired compound of formula (I). Pharmaceutically and veterinarily acceptable salts include acid addition salts with pharmaceutically or veterinarily acceptable acids, including hydrochloric, hydrobromic, hydroiodic, nitric, sulphuric, citric, lactic, maleic, pamoic and tartaric acids.

Particularly suitable compounds of formula (I) include:
3-amino-2,6-dichlorobenzylideneamino guanidine
4-amino-2,6-dichlorobenzylideneamino guanidine
3-amino-2,6-dichlorophenylacetyl guanidine
4-amino-2,6-dichlorophenylacetyl guanidine
and their mono- or di-hydrohalide salts, especially their mono- or di-hydrochloride salts.

The present invention also provides a process for producing compounds of formula (I) which process comprises either:

(a) reducing a compound of formula (II):

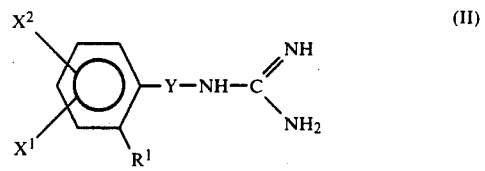

wherein
$X^1$ is a nitro or a group $R^2$, and
$X^2$ is nitro or a group $R^3$,
provided that at least one of $X^1$ and $X^2$ is nitro, and $R^1$, $R^2$, $R^3$ and Y are as defined with respect to formula (I),
to produce a compound of formula (I) wherein $R^2$ and/or $R^3$ is amino and $R^4$ is hydrogen;
or (b) condensing a compound of formula (III):

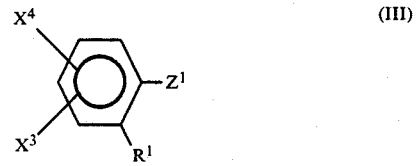

wherein
$X^3$ is a group $R^2$ or a protected derivative thereof, and
$X^4$ is a group $R^3$ or a protected derivative of a nitrogen-containing basic substituent,
$Z^1$ is CHO or $CH_2CO_2R^5$, and
$R^1$, $R^2$ and $R^3$ are as defined with respect to formula (I), and
$R^5$ is $(C_{1-4})$alkyl or optionally substituted benzyl; with the compound of formula (IV):

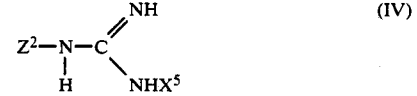

wherein
$Z^2$ is hydrogen when $Z^1$ is —$CH_2CO_2R^5$ or $Z^2$ is amino when $Z^1$ is —CHO, and $X^5$ is hydrogen hydroxy or protected hydroxy;
or a protected derivative thereof, or a salt of the compound where $Z^2$ is amino or derivative thereof, and, where necessary, thereafter removing any protecting groups from the compound of formula (I) so produced, and optionally thereafter converting the compound of formula (I) so produced into a further compound of formula (I).

Reduction of a compound of formula (II) may be effected by conventional methods, such as chemical reduction using suitable reducing agents, for instance tin chloride. Suitably, reduction with tin chloride is effected in a mixture of hydrochloric and glacial acetic acid at elevated temperature.

Condensation of a compound of formula (III) with the compound of formula (IV) may be effected under conventional conditions, such as in an organic solvent at a temperature up to the boiling point of the reaction mixture. Suitably the solvent is ethanol. Suitable salts of the compound of formula (IV) include the hydrohalide and hydrogen carbonate.

As used herein the term "protected derivative" refers to a derivative of a compound having one or more N-H groups wherein the hydrogen atom is replaced by a protecting group to prevent undesired reaction at the nitrogen atom. Suitable protecting groups, which include ($C_{1-4}$) alkanoyl and optionally substituted benzyl and benzoyl groups, are readily removed by conventional methods after the desired reaction has taken place. A particularly convenient protecting group is the acetyl group, which may be readily removed by mild acid hydrolysis.

As used herein the term "protected hydroxy" refers to a group which is stable during the condensation reaction between compounds of formulae (III) and (IV) but which may readily be converted to hydroxy thereafter. Suitable protected hydroxy groups include silyoxy especially trimethylsilyoxy groups.

Compounds of formula (I) may be converted into further compounds of formula (I) by conventional methods, such as alkylation or acylation of an N-H group.

Salts of compounds of formula (I) may be produced by conventional methods.

Compounds of formula (II) may be produced by conventional methods. Thus, for instance a compound of formula (V):

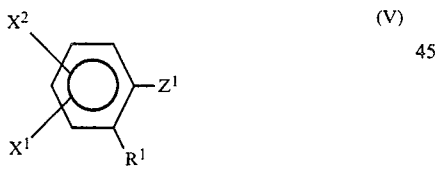

may be condensed with a compound of formula (IV) above by methods similar to those used to condense compounds of formulae (III) and (IV). In compounds of formulae (V) the groups $R^1$, $X^1$, $X^2$ and $Z^1$ are as hereinbefore defined.

Alternatively compounds of formula (II) may be produced by nitration of the corresponding compound lacking the nitro group(s) $X^1$ and/or $X^2$.

Compounds of formula (III) wherein $Z^1$ is —CHO may be produced by conventional methods, for instance by the route shown in Scheme I below. For simplicity Scheme I shows the details for producing compounds of formula (III) wherein $X^3$ is amino and $X^4$ is a group $R^3$ in the ortho position with respect to $Z^1$. Similar procedures may be used to produce other compounds of formula (III). Suitable reagents and conditions are exemplified below.

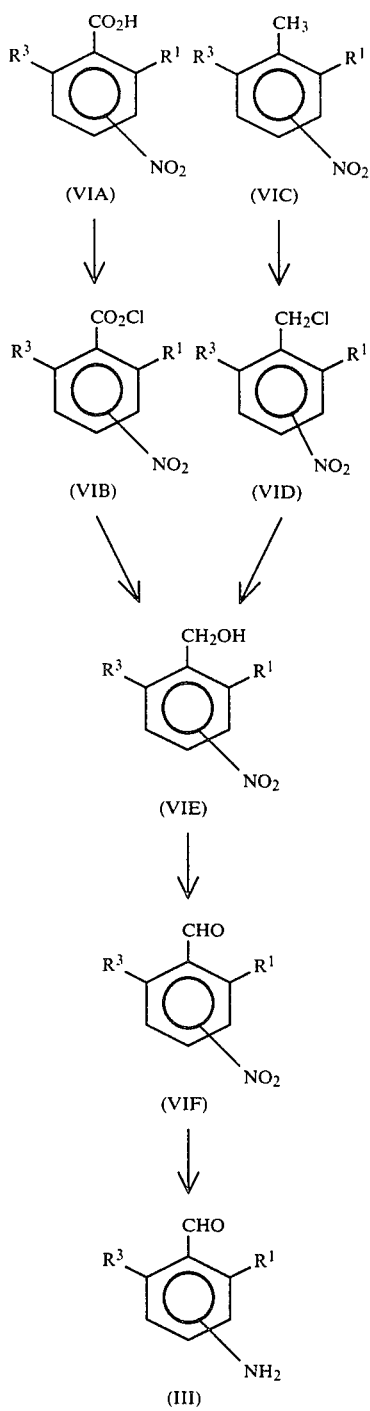

The compounds of formulae (VID) and (VIE) in Scheme I are novel and are useful as intermediates in producing compounds of formula (I).

Accordingly the present invention provides, in a further aspect, a compound of formula (VI):

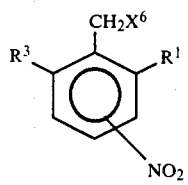

(VI)

wherein $R^1$ and $R^3$ are as defined with respect to compounds of formula (I) and $X^6$ is halogen or hydroxy.

Compounds of formula (III) wherein $Z^1$ is $CH_2CO_2R^4$ may be produced by conventional methods such as those shown in Scheme 2 below. Suitable reagents and conditions are exemplified below.

Compounds of formulae (IV), (VIA), (VIC), (VIIA), and (VIIE) are known and readily available or may be produced by known methods.

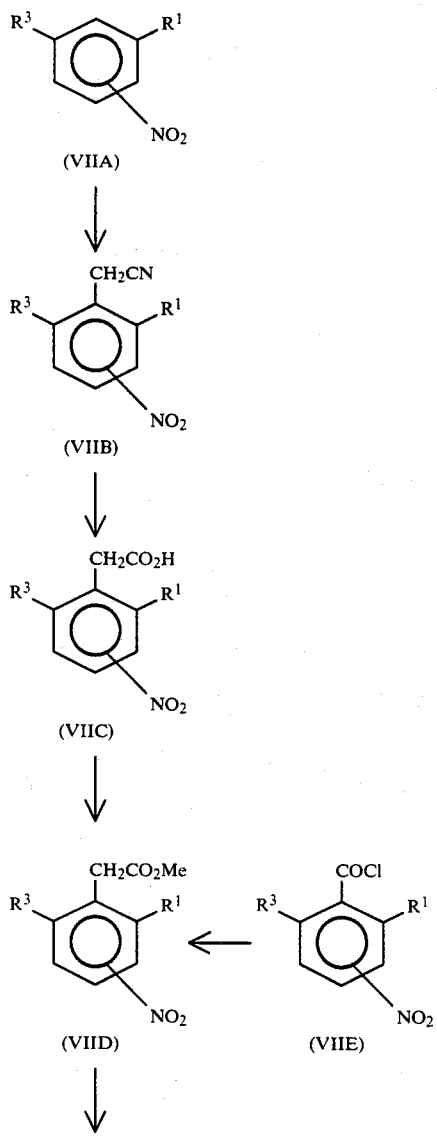

Scheme 2

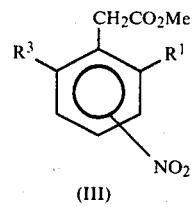

(III)

Compounds of formula (I) inhibit enterotoxin-induced secretion into the small intestine, and are useful in treatment of enterotoxin induced diarrhoea in humans and scours in animals, especially diarrhoea or scours caused by enteropathogenic strains of *Escherichia coli* which produce heat stable and/or heat labile enterotoxins. Related enterotoxins are produced by other enteropathogens, for example, cholera, and also cause diarrhoea which may also be treated using compounds of formula (I).

The present invention therefore provides a compound of formula (I) for use in human or veterinary medicine.

The present invention further provides a pharmaceutical or veterinary composition comprising a compound of formula (I) (hereinafter referred to as the "drug") and a pharmaceutically or veterinarily acceptable carrier therefor.

Pharmaceutical and veterinary compositions of the drug will, of course, be adapted for administration to the humans or animals to be treated. Thus, for example, the composition may be a shaped composition, such as a bolus, tablet or capsule. In such cases the pharmaceutically or veterinarily acceptable carrier will be chosen from the usual range of lubricants, dispersants, binders, fillers and the like. When these shaped compositions are for administration to cattle and pigs often they will weigh at least 1 g, on occasions at least 2 g.

For administration to humans, especially children, the drug may suitably be presented as a syrup including suitable colouring and/or flavouring agents. Such syrups are conveniently presented in unit or multi-dose containers.

For veterinary use the composition may also be a dispersion or a solution of the drug in a suitable vehicle for use with an oral doser (this is a well known item of farm equipment, basically comprising a liquid reservoir, a mouthpiece adapted for insertion into animals mouths, and a pump mechanism whereby unit doses can be ejected form the reservoir through the mouthpiece). Conveniently the drug may be administered from an oral doser as an aqueous solution. Alternatively, the vehicle will be an oil or water based cream to ensure homogeneity of the unit doses administered.

The invention, therefore, also provides an oral doser containing a multi-dose of the drug in a veterinarily acceptable vehicle.

The drugs of the invention may also be added to the animal feed or drinking water. Thus the invention also provides animal feed or animal drinking water containing a compound of formula (I). It will be convenient to formulate these animal feed and drinking water compositions with a multi-dose of the drug so that the animal takes in an appropriate quantity of the drug along with its diet. It will also be convenient to present the composition of the invention as a pre-mix for addition to the feed or drinking water.

With human babies or young animals, a particularly useful technique is to blend their milk with the drugs of this invention.

The compositions of the invention may also be formulated for injection. In such cases the drug chosen is suitably dissolved in water for injection.

Often will be appropriate to include in the compositions a further medicine such as an antibacterial agent for example an antibiotic such as amoxycillin or neomycin or a sulphonamide such as sulfadoxin.

Treatment of diarrhoea and scours using the drug may be supplemented by oral rehydration therapy such as those described in U.K. Pat. No. 1,581,826 and German Offenlegungsschrift No. 28 54 281, U.K. Patent Application No. 2 012 163A, U.S. Pat. No. 3,898,328, Nalin, D. R. and Cash. R. A., Bull. World Health Org., 43, 361 (1970), French Pat. No. 2 467 599, U.K. Pat. No. 1 465 308 and as described in "Secretory Diarrhoea", Ed M. Field, J. S. Fordtran and S. G. Schultz, American Physiological Society, Maryland, 1980 pp 179-185 and Lancet, (1975) pp 79 and 80. Conveniently the drug may be administered with the oral rehydration formulation. Alternatively it may be provided separately and administered simultaneously or sequentially with the oral rehydration formulation.

The amount of drug administered must, of course, be sufficient to bring about the desired effect and will also depend on the body weight of the recipient and the chosen route of administration. Thus, by way of example, useful dosage units of the composition for treating diarrhoea may contain 1 µg to 50 mg of the drug, most suitably 20 µg to 20 mg. Of course, it will be appreciated that many preferred compositions of the invention are in multi-dose form as, for the therapy of animals, it is often most desirable to be able rapidly to treat a number of animals. Such multi-dose compositions will contain, by way of example, at least 1 mg of the drug. Depending on the exact nature of the said multi-dose composition, often it will contain at least 50 mg of the drug, and on occasions as much as 1 g. Doses may be administered once or several times daily.

The present invention further provided a method for treating humans and animals, which method comprises administering an effective, non-toxic amount of a compound of formula (I) to the sufferer. Such treatment may be sedation, vasoconstriction, or a treatment for diarrhoea or hypertension.

In a particular aspect the method of treatment comprises the administration of a pharmaceutical or veterinary composition of a compound of formula (I), as hereinbefore described.

The present invention will now be illustrated by the following Examples which are not intended to limit the invention in any way.

EXAMPLE 1

(2,6-dichloro-4-dimethylaminobenzylideneamino)-guanidine hydrochloride (a) 3,5-dichloro-N,N-dimethylaniline Glacial acetic acid (1.85 cm$^3$) was added dropwise to a stirred mixture of aqueous formaldehyde (37-40%, 15 cm$^3$), sodium cyanoborohydride (3.5 g, 56 mmol) and 3,5-dichloroaniline (3.0 g, 18.5 mmol) in acetonitrile (75 cm$^3$). The mixture was stirred for 3 h at room temperature, diluted with diethyl ether (200 cm$^3$) and extracted with dilute sodium hydroxide solution (3×70 cm$^3$) then brine. The dried organic extract was evaporated to an oil to which acetone (20 cm$^3$) and concentrated hydrochloric acid (1.7 cm$^3$) were added. The resulting white solid was collected and rebasified by dissolving in water and extracting the solution with diethyl ether. After drying and evaporation of the organic extract, a colourless oil was obtained and identified as 3,5-dichloro-N,N-dimethylaniline.

$^1$Hnmr (60 MHz)

H (CDCl$_3$) 6.60 (m, 3$\underline{H}$, Ar—$\underline{H}$), 2.90 ppm (S, 6$\underline{H}$, 2Me).

(b) 2,6-dichloro-4-dimethylaminobenzaldehyde

Phosphoryl chloride (0.56 cm$^3$, 6.1 mmol) was added dropwise to cooled N,N-dimethyl formamide (4 cm$^3$) under nitrogen. 3,5-dichloro-N,N-dimethylaniline (1.16 g, 6.1 mmol) was then added to the solution which was then heated under nitrogen at 100° C. for 3 h. The solution was cooled, poured onto ice (6 g) and the mixture adjusted to pH 6 by addition of a saturated solution of sodium acetate. The suspended solid was collected and recrystallised from ethyl acetate-petroleum spirit 60°-80° C. mixture giving pale yellow needles of 2,6-dichloro-4-dimethylaminobenzaldehyde (0.8 g) mp 169°-71° C.

$^1$Hnmr (60 MHz)

H (CDCl$_3$) 10.37 (S, 1$\underline{H}$, C$\underline{H}$O), 6.5, 2$\underline{H}$, Ar—$\underline{H}$), 3.05 ppm (S, 6$\underline{H}$, 2Me);

ir spectrum (KBr disc)

1675 cm$^{-1}$ (CO).

(c)

(2,6-dichloro-4-dimethylaminobenzylideneamino)-guanidine hydrochloride

Aminoguanidine hydrogen carbonate (474 mg, 3.5 mmol) was added to a solution of concentrated hydrochloric acid (0.3 cm$^3$) in water (1 cm$^3$). After diluting the resulting solution with ethanol (14 cm$^3$) 2,6-dichloro-4-dimethylaminobenzaldehyde (760 mg, 3.5 mmol) was added and the solution was heated under reflux for 54 h. The cooled mixture was evaporated to a solid which was triturated with dichloromethane, the solid was collected and recrystallised from ethanol-diethyl ether mixture affording (2,6-dichloro-4-dimethylaminobenzylideneamino)-guanidine hydrochloride as a white solid (650 mg) m.p. 255°-6° C.

Analysis: calculated for C$_{10}$H$_{14}$Cl$_3$N$_5$ Theory: C, 38.67; H, 4.54; N, 22.55%, Found: C, 38.66; H, 4.25; N, 22.58.

EXAMPLE 2

(3-amino-2,6-dichlorobenzylideneamino)-guanidine dihydrochloride (a) (2,6-dichloro-3-nitrobenzylideneamino)-guanidine hydrochloride Aminoguanidine hydrogen carbonate (1.24 g, 9.1 mmol) was added to a solution of concentrated hydrochloric acid (0.8 cm$^3$, 9.3 mmol) in water (3 cm$^3$). After diluting the resulting solution with ethanol (20 cm$^3$), 2,6-dichloro-3-nitrobenzaldehyde (2.0 g, 9.1 mmol) was added and the mixture heated under reflux for 7 h. The solution was evaporated under reduced pressure and the residual solid suspended in refluxing ethanol, basified (pH 11) by addition of dilute sodium hydroxide solution and cooled to yield a white solid which was collected. This solid was dissolved in hot methanol and the solution acidified (pH 2) with ethanolic hydrogen chloride, diluted with diethyl ether and cooled to yield (2,6-dichloro-3-nitrobenzylideneamino)-guanidine hydrochloride as a white solid, m.p. 186°-7° C.

Analysis: calculated for $C_8H_8Cl_3N_5O_2$ Theory: C, 30.74; H, 2.58; Cl, 34.03; N, 22.41%, Found: C, 30.51; H, 2.43; Cl, 33.70; N, 22.11%.

(b) (3-amino-2,6-dichlorobenzylideneamino)-guanidine dihydrochloride

A hot solution of stannous chloride dihydrate (12.8 g, 56.7 mmol) in concentrated hydrochloric acid (15 cm³) was slowly added to a hot stirred solution of (2,6-dichloro-3-nitrobenzylideneamino)-guanidine (2.0 g, 7.2 mmol) in glacial acetic acid (20 cm³). The solution was cooled and the precipitated white solid collected, dissolved in methanol (30 cm³) and the solution saturated with hydrogen sulphide. After filtering off the inorganic salts the filtrate was concentrated and then diluted with diethyl ether to yield a white solid which was recrystallised from methanol-diethyl ether affording (3-amino-2,6-dichlorobenzylideneamino)-guanidine dihydrochloride (1.4 g) m.p. 218°-220° C. (dec).

Analysis: calculated for $C_8H_{11}Cl_4N_5$, Theory: C, 30.12; H, 3.48; Cl−, 22.22; N, 21.95%, Found: C, 30.17; H, 3.50; Cl−, 21.94; N, 21.90%.

EXAMPLE 3

(4-Amino-2,6-dichlorobenzylideneamino)-guanidine dihydrochloride (a) 2,6-dichloro-4-nitrobenzoylchloride A mixture of 2,6-dichloro-4-nitrobenzoic acid (1.53 g, 6.5 mmol), thionyl chloride (1.0 cm³, 13.7 mmol) and N,N-dimethylformamide (0.1 cm³) were heated under reflux for 1.5 h. The mixture was evaporated under reduced pressure to an oil which was purified by evaporative distillation yielding 2,6-dichloro-4-nitrobenzoyl chloride as a pale yellow oil (1.37 g, bp 140° C. at 0.2mm Hg) which solidified with cooling. (mp 63°-5° C.).

¹Hnmr (60 MHz) H (CDCl₃)
8.34 ppm (S, ArH)
ir spectrum (liquid)
1794 cm⁻¹ (CO).

(b) 2,6-dichloro-4-nitrobenzylalcohol

Lithium aluminium hydride (400 mg, 10.4 mmol) was added in portions to a stirred solution of 2,6-dichloro-4-nitrobenzoyl chloride (3.0 g, 11.8 mmol) in diethyl ether (50 cm³) at room temperature. After 1.5 h the mixture was poured onto ice (80 g), acidified with 10% sulphuric acid (80 cm³) and extracted with ethyl acetate (3×60 cm³). The dried organic extracts were evaporated to an oil which was purified by chromatography over silica gel with a methanol-dichloromethane solvent gradient. The fractions containing 2,6-dichloro-4-nitrobenzylalcohol, were combined and evaporated under reduced pressure to a give a cream solid mp 111°-4° C. (0.7 g).

¹Hnmr (60 MHz) H (CDCl₃)
8.20 (S, 2H, ArH), 5.0 (S, 2H, 2.25 ppm (br, s, 1H, OH).

(c) 2,6-dichloro-4-nitrobenzaldehyde

A solution of dimethyl sulphoxide (1.2 cm³) in dichloromethane (5 cm³) was added dropwise to a stirred solution of oxalyl chloride (0.7 cm³, 8.0 mmol) in dichloromethane (12 cm³) at −60° C. under nitrogen. After 10 mins at −60° C. a solution of 2,6-dichloro-4-nitrobenzylalcohol (1.53 g, 6.9 mmol) in dichloromethane (10 cm³) was added dropwise and the stirred mixture kept at −60° C. for 0.5 h. Triethylamine (4.6 cm³, 33 mmol) was then added and the mixture was allowed to warm to room temperature at which stage water (35 cm³) was added. The heterogeneous mixture was separated and the aqueous phase extracted with dichloromethane (35 cm³). The combined organic fractions were extracted with hydrochloric acid (2M, 60 cm³), then water (60 cm³), saturated sodium carbonate solution (60 cm³), and finally water (60 cm³) then dried and evaporated under reduced pressure to give 2,6-dichloro-4-nitrobenzaldehyde as a pure oil which slowly solidified.

¹Hnmr (90 MHz) H (CDCl₃)
10.50 (S, 1H, CHO), 8.28 (S, 2H, Ar—H).
ir spectrum (oil)
1710 cm⁻¹ (CO).

(d) (2,6-dichloro-4-nitrobenzylideneamino)-guanidine hydrochloride

Aminoguanidine hydrogen carbonate (0.96 g, 7.0 mmol) was added to a solution of concentrated hydrochloric acid (0.6 cm³) in water (2 cm³). After diluting the resulting solution with ethanol (20 cm³), 2,6-dichloro-4-nitrobenzaldehyde (1.53 g, 7.0 mmol) was added and the suspension heated under reflux for 2.5 h. The reaction mixture was cooled and diluted with diethyl ether to yield (2,6-dichloro-4-nitrobenzylidene amino)-guanidine hydrochloride as a yellow solid, mp 190° C. (dec).

¹Hnmr (60 MHz) H [(CD₃)₂SO-D₂O]
8.46 (S, 1H, CHO), 8.35 ppm (S, 2HH).

(e) (4-amino-2,6-dichlorobenzylideneamino)-guanidine dihydrochloride

A hot solution of stannous chloride dihydrate (7.8 g, 35 mmol) in concentrated hydrochloric acid (9 cm³) was slowly added to a hot stirred solution of (2,6-dichloro-3-nitrobenzylideneamino)-guanidine hydrochloride (1.22 g, 3.9 mmol) in glacial acetic acid (18 cm³). The solution was chilled and the precipitated solid collected, dissolved in methanol and the solution saturated with hydrogen sulphide. After filtering off the inorganic salts, the filtrate was evaporated in vacuo and the residue converted to the conjugate base by ion-exchange chromatography using methanol as eluant. The total fraction was collected, evaporated under reduced pressure and the residue chromatographed over alumina with a dichloromethane-methanol-ammonia (S.G=0.880) gradient eluant. The desired fractions were combined, evaporated and the residue acidified with excess ethanolic hydrogen chloride affording (4-amino-2,6-dichlorobenzylideneamino)-guanidine dihydrochloride as a cream solid mp 228° C. (dec).

¹H nmr (60 HHz) H [(CD₃)₂SO]
12.3 (br, s, 1H, N+H), 8.30 (S, 1H, CH=N), 7.60 (br, s, 4H, NH) 6.70 (S, 2H, Ar—H), 4.7 ps, NH).

EXAMPLE 4

(3-Amino-2,6-dichlorophenylacetyl)-guanidine dihydrochloride (a) (2,6-dichloro-3-nitrophenylacetyl)-guanidine Concentrated sulphuric acid (25 cm³) was added dropwise to cooled concentrated nitric acid (25 cm³), followed by (2,6-dichlorophenylacetyl)-guanidine (2.5 g 8.9 mmol) and the mixture stirred at 0° to 5° C. for 2.5 h. After pouring onto ice (600 g) the mixture was neutralised with sodium hydroxide solution and the precipitated cream solid collected and recrystallised from aqueous methanol affording pale yellow plates of (2,6-dichloro-3-nitrophenylacetyl)-guanidine (2.1 g) m.p. 198°-9° C. (dec). The corresponding hydrochloride was prepared by dissolving the base in hot ethanolic hydrogen chloride. The cooled solution yielded the hydrochloride as a white solid.

$^1$Hnmr (60 MHz) H [(CD$_3$)$_2$SO]
7.95 (m, 2H, Ar;H), 6.70 (br, s, 4H, NH), 4.32 ppm (S, 2H, CH$_2$).

(b) (3-Amino-2,6-dichlorophenylacetyl)-guanidine dihydrochloride

A hot solution of stannous chloride dihydrate (9 g, 40 mmol) in concentrated hydrochloric acid (10.5 cm$^3$) was slowly added to a hot, stirred solution of (2,6-dichloro-3-nitrophenylacetyl)-guanidine (1.5 g, 5.2 mmol) in glacial acetic acid (15 cm$^3$) and the mixture left to stand overnight then cooled and adjusted to pH 6 by addition of an ice and aqueous sodium hydroxide mixture. The precipitated white solid was separated, dissolved in methanol and the solution saturated with hydrogen sulphide. After filtering off the inorganic salts the methanolic filtrate was concentrated, basified with sodium hydroxide (2M) solution and the resulting solid collected, then dissolved in excess hot ethanolic hydrogen chloride to yield, after cooling, (3-amino-2,6-dichlorophenylacetyl)-guanidine dihydrochloride as a white solid, m.p. 237° C.

Analysis: calculated for C$_9$H$_{12}$Cl$_4$N$_4$O, Theory: C, 32.36; H, 3.62; N, 16.77%, Found: C, 32.68; H, 3.25; N, 16.42%.

EXAMPLE 5

(4-Amino-2,6-dichlorophenylacetyl)-guanidine dihydrochloride (a) Methyl-(2,6-dichloro-4-nitrotoluene)-carboxylate A solution of diazomethane in diethylether was prepared by adding N-nitrosomethylurea (8.0 g, 78 mmol) in portions to a stirred mixture of potassium hydroxide solution (40%, 30 cm$^3$) and diethylether (80 cm$^3$) at −10° C. The ether layer was then decanted onto fresh potassium hydroxide pellets and left to stand at −25° C. for 2 h. The solution was then again decanted from the solid and to the solution at −20° C. was added with stirring a solution of 2,6-dichloro-4-nitrobenzoylchloride (2.5 g, 9.8 mmol) in diethyl ether (30 cm$^3$). The reaction mixture was maintained at −20° C. for 2.5 h then allowed to warm to room temperature and left to stand overnight. The solvent was then evaporated under reduced pressure to leave an oil to which methanol (60 cm$^3$) and freshly prepared silver oxide (600 mg) were added. The resulting suspension was then heated at 60° C. for 2 h. The mixture was filtered warm, washed with methanol and the filtrate evaporated under reduced pressure to give an oil which was chromatographed over silica gel eluting with an ethyl acetate-petroleum ether 60°-80° C. gradient. Fractions containing the desired material were combind and evaporated to yield yellow prisms of methyl-(2,6-dichloro-4-nitrotoluene)-carboxylate (1.65 g) mp 63°-5° C.

$^1$H nmr (60 MHz) H (CDCl$_3$)
8.20 (S, 2H, Ar—H), 4.08 (S, 2H, CH$_2$), 3.72 ppm (S, 3H, Me).

ir spectrum (mull)
1738 cm$^{-1}$ (CO).

(b) Methyl-(4-amino-2,6-dichlorotoluene)-carboxylate

Concentrated hydrochloric acid (0.28 cm$^3$) was added to a mixture of methyl-(2,6-dichloro-4-nitrotoluene)-carboxylate (2.87 g, 10.9 mmol), iron powder (3.8 g), water (16 cm$^3$) and methanol (16 cm$^3$) previously heated to reflux. The temperature was maintained for 1.5 h, cooled to 65° C. for 1.5 h, and the iron residues filtered and washed with methanol (2×15 cm$^3$) and dichloromethane (4×40 cm$^3$). The filtrate was then extracted with saturated sodium bicarbonate solution (50 cm$^3$), dried and evaporated under reduced pressure to give methyl-(4-amino-2,6-dichlorotoluene)-carboxylate as a pure oil (2.53 g), which was used as such in the next stage.

ir spectrum (oil)
3475 and 3380 (NH), 1730 (CO).

(c) (4-Amino-2,6-dichlorophenylacetyl)-guanidine dihydrochloride

A mixture of methyl-(4-amino-2,6-dichlorotoluene)-carboxylate (2.53 g, 10.8 mmol), guanidine (1.0 g, 16.3 mmol) and methanol (40 cm$^3$) were heated at reflux under nitrogen for 34 h. The solvent was then evaporated under reduced pressure and the residue stirred with a chloroform-water mixture (30:30 cm$^3$). The suspended solid was filtered, dissolved in hot ethanolic hydrogen chloride and the solution cooled to yield a solid which was recrystallised from methanol-diethylether affording (4-amino-2,6-dichlorophenylacetyl)-guanidine dihydrochloride as needles, mp 249° C. (dec).

$^1$H nmr (60 MHz) H [(CD$_3$)$_2$SO-D$_2$O]
6.80 (S, 2H, Ar—H), 3.92 ppm (S, 2H, CH$_2$).

Analysis: calculated for C$_9$H$_{12}$Cl$_4$N$_4$O, Theory: C, 32.36; H, 3.62; N, 16.77%, Found: C, 32.87; H, 3.67; N, 16.49%, The chloroform fraction of the filtrate was dried and evaporated to yield unreacted methyl-(4-amino-2,6-dichlorotoluene)-carboxylate (0.8 g).

EXAMPLE 6

Alternative route to 2,6-dichloro-4-nitrobenzylalcohol (cf Example 3)

(a) 2,6-Dichloro-4-nitrobenzylchloride

A solution of 2,6-dichloro-4-nitrotoluene (2.0 g 9.7 mmol) in tetrahydrofuran: methanol mixture (20:11 cm$^3$) was added slowly to a vigorously stirred solution of 10–14% aqueous sodium hypochlorite (15 cm$^3$) at 0° C. After 3.75 h at this temperature, the mixture was poured into dilute hydrochloric acid and then extracted with chloroform (30 cm$^3$). The organic extract was dried and evaporated to yield an organge oil which was purified by flash chromatography over silica gel eluting with an ethyl acetate-petroleum ether gradient. The title compound was obtained as a pale orange solid, m.p. 37°-9° C. (1.8 g).

$^1$Hnmr (60 MHz) δH(CDCl$_3$)
8.20 (S, 2H, Ar—H), 4.85 ppm (S, 2H, CH$_2$)

(b) 2,6-Dichloro-4-nitrobenzylalcohol

A suspension of silver carbonate (560 mg), 2,6-dichloro-4-nitrobenzylchloride (440 mg) in 2-methoxyethanol (9 cm$^3$) and water (9 cm$^3$) were heated at reflux for 18 h. After this time the hot reaction mixture was filtered and the filtrate diluted with dichloromethane (30 cm$^3$) and water (20 cm$^3$). The heterogeneous mixture was shaken, separated and the aqueous phase extracted with dichloromethane (30 cm$^3$). Combined organic extracts were washed with saturated brine, dried and evaporated to leave an orange oil which was purified by chromatography over silica gel with an ethyl acetate—petroleum ether gradient. The title compound was obtained as a cream solid, m.p. 111°–114° C.

EXAMPLE 7

Alternative route to Methyl-(2,6-dichloro-4-nitrotoluene)carboxylate (cf Example 5).

(a) 2,6-Dichloro-4-nitrobenzylnitrile (Methylthio)acetonitrile (43.7 cm$^3$) was added to a stirred solution of 1,3-dichloro-5-nitrobenzene (100 g) in dimethylsulphoxide (800 cm$^3$) under nitrogen. Powdered sodium hydroxide (41.7 g) was then added to the mixture in a single portion with initial cooling. After 24 h stirring at room temperature, water (500 cm$^3$) was added to the cooled mixture followed by dilute hydrochloric acid (700 cm$^3$) until pH 1 was attained. The dark mixture was partitioned between diethyl ether-dichloromethane (1:1 by volume, 1 liter) and water (1 liter). The layers were separated and the organic phase further extracted with water (3×500 cm$^3$) then dried and evaporated to a viscous oil. The oil was purified by chromatography over silica gel with an ethyl acetate—petroleum ether gradient to yield a tanned solid, m.p. 102°–4° C. (38 g).

$^1$Hnmr (90 MHz) δH (CDCl$_3$)
8.30 (S, 2$\underline{H}$, Ar—$\underline{H}$), 4.10 ppm (S, 2$\underline{H}$, C$\underline{H}_2$)
ir spectrum y(KBr)
2250 cm$^{-1}$ (CN)

(b) 2,6-Dichloro-4-nitrophenylacetic acid

A stirred suspension of 2,6-dichloro-4-nitrobenzylnitrile (420 mg) in concentrated sulphuric acid (1.7 cm$^3$) and water (2 cm$^3$) was heated for 2.5 h at 150° C. The reaction mixture was then poured into water (12 cm$^3$) and the precipitated white solid collected and recrystallised (ethanol—water) to yield the title compound as cream microneedles, m.p. 206°–7° C. (450 mg).

$^1$Hnmr (60 MHz) δH [(CD$_3$)$_2$SO]
8.30 (S, 2$\underline{H}$, Ar—$\underline{H}$), 4.0 ppm (S, 2$\underline{H}$, C$\underline{H}_2$).
ir spectrum y(KBr)
1705 cm$^{-1}$ (CO).

(c) Methyl-(2,6-dichloro-4-nitrotoluene)-carboxylate

A solution of 2,6-dichloro-4-nitrophenylacetic acid (10 g) in methanol (300 cm$^3$) and concentrated sulphuric acid (11 cm$^3$) was heated under reflux for 2.5 h. The mixture was cooled, diluted with a solution of sodium carbonate until pH 8 was attained and then extracted with dichloromethane (3×150 cm$^3$). The combined organic extracts were dried and evaporated to a pale yellow solid, m.p. 63°–5° C. (9.9 g) identified as the title compound.

Biological Evaluation of the Compounds (i) Inhibition of enterotoxin-induced secretion The following test was carried out in mice:
7-9 Day old infant mice are separated from their mothers shortly before use and are administered the compound 45 minutes prior to oral challenge with 0.05-0.1 ml of culture filtrate prepared from an enteropathogenic strain of E.coli. Control animals receive drug vehicle 45 minutes prior to challenge with a similar amount of culture filtrate. The compounds are administered orally. Animals are killed two hours later and the entire intestine removed. The ratio of gut weight to remaining bodyweight (GW/BW) is determined from each animal and the increase in this ratio is determined by subtracting 0.06 (GW/BW for untreated mice) from the GW/BW of the animal. Drug treated animals are compared with untreated controls. If the compound has had an effect in inhibiting the fluid secretion caused by the enterotoxin(s) present in the culture filtrate then the gut weight/bodyweight ratio should be reduced in the treated animals. The percentage fluid inhibition is determined from the formula:

$$100 - \frac{\text{Mean increase in } GW/BW \text{ ratio in treated animals}}{\text{Mean increase in } GW/BW \text{ ratio in control animals}} \times$$

Results are given in Table I.

TABLE I

Activity of Compounds against ST in mice

| Compound of Example No. | R | X | Y | Z | Dose mg/kg | % inhibition ST Mouse |
| --- | --- | --- | --- | --- | --- | --- |
| 5 | Cl | m-NH$_2$ | CH$_2$CO | 2HCl | 200 | 75* |
|   |    |          |          |      | 50  | 57* |
|   |    |          |          |      | 10  | 49* |
|   |    |          |          |      | 1   | 16  |
| 4 | Cl | p-NH$_2$ | CH$_2$CO | 2HCl | 50  | 66* |
|   |    |          |          |      | 10  | 60* |
|   |    |          |          |      | 2   | 25* |
| 1 | Cl | pNMe$_2$ | CH=N     | HCl  | 10  | 37* |
|   |    |          |          |      | 1   | 36* |
| 2 | Cl | mNH$_2$  | CH=N     | 2HCl | 200 | 69* |
|   |    |          |          |      | 50  | 44* |
|   |    |          |          |      | 10  | 53* |
| 3 | Cl | pNH$_2$  | CH=N     | 2HCl | 50  | 61* |
|   |    |          |          |      | 10  | 49* |

*Indicates statistically significant effect at least P 0.05 students t test.

(ii) Protection of Neonatal Mice from Lethal Enteropathogenic E coli Infection 4 day old mice were orally dosed with 50 μl of phosphate buffered saline containing 1×10$^5$ organisms/ml of E coli B44 (09:K90:K99) an enteropathogenic strain originaly isolated from a scouring calf. The mice were then dosed b.i.d. with either placebo or drug for four days commencing 16 hours after infection. The animals were left with their mothers throughout the experiment and a daily record of deaths was made. The experiment was terminated 10 days after infection. The mortality in the drug was then compared with the mortality in the placebo group using the following formula:

$$\% \text{ Reduction in mortality} = \frac{Mp - Md}{Mp} \times 100$$

where
Mp=mortality in group receiving placebo
Md=mortality in group receiving drug
Statistical analysis was performed using 2×2 contingency tables (single tailed 'p'). Results are given in Table 2.

TABLE 2

Reduced Mortality in *E. coli* Infected Mice Dosed with the compound of Example 5

| Treatment | | No. of mice infected | Mortality | % protection |
|---|---|---|---|---|
| Compound of Example 5 | 0.4 mg/kg | 72 | 39/72 | 22% |
| | Control | 73 | 51/73 | (P=0.05) |
| Compound of Example 5 | 0.08 mg/kg | 72 | 34/72 | 31% |
| | Control | 72 | 49/72 | (P 0.05) |

(iii) Calf Tolerance of the compound of Example 5

The compound of Example 5 was dosed orally to approximately 10 day old calves purchased at market. No adverse symptons were observed following doses of 0.08, 0.4 or 2 mg/kg.

We claim:

1. A compound of formula (I):

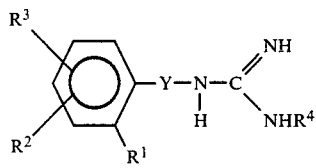

or a salt or acyl derivative thereof;
wherein
Y is

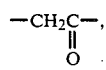

$R^1$ is hydroxy, halogen, $(C_{1-4})$ alkyl, or $(C_{1-4})$alkoxy,
$R^2$ is a nitrogen-containing, basic, substituent selected from the group consisting of amino, mono- or di-$(C_{1-4})$ alkylamino, aminomethyl, mono- or di-$(C_{1-4})$ alkyl-aminomethyl, amidino, guanidino and 2-imidazolino, said guanidino and 2-imidazolino being unsubstituted or substituted on a nitrogen atom thereof by $C_{1-4}$ alkyl, $C_{1-4}$ alkanoyl, benzoyl or benzoyl substituted by $C_{1-4}$ alkyl, $C_{1-4}$ alkoxy or amino,
$R^3$ is hydrogen, hydroxy, halogen, $(C_{1-4})$ alkyl, $(C_{1-4})$ alkoxy or a nitrogen-containing, basic substituent selected from the group consisting of amino, mono- or di-$(C_{1-4})$alkylamino, aminomethyl, mono- or di-$(C_{1-4})$ alkylaminomethyl, amidino, guanidino and 2-imidazolino, said guanidino and 2-imidazolino being unsubstituted or substituted on a nitrogen atom thereof by $C_{1-4}$ alkyl, $C_{1-4}$ alkanoyl, benzoyl or benzoyl substituted by $C_{1-4}$ alkyl, $C_{1-4}$ alkoxy or amino, and $R^4$ is hydrogen or hydroxy.

2. A compound as claimed in claim 1 wherein $R^1$ and $R^3$ are the same and each is chlorine or methyl.

3. A compound as claimed in claim 1 wherein $R^2$ is situated in the meta position with respect to group Y.

4. A compound as claimed in claim 1 wherein $R^3$ is situated in the ortho position with respect to the group Y.

5. A compound as claimed in claim 1 wherein $R^2$ is amino or dimethylamino.

6. A compound according to claim 1, wherein $R^1$ and $R^3$ are halogen.

7. A compound according to claim 1, which is 3-amino- or 4-amino-2,6-dichlorophenylacetyl guanidine.

8. A pharmaceutical or veterinary composition in unit dose form for treating diarrhoea and scours in human and non-human animals, comprising per unit dose from 1 mg to 50 mg of a compound of formula (I):

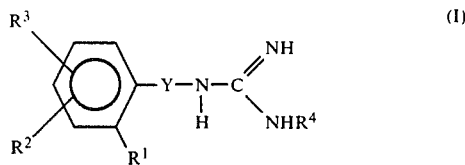

or a salt or acyl derivative thereof;
wherein Y is either —CH=N— or

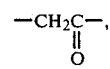

$R^1$ is hydroxy, halogen, $(C_{1-4})$ alkyl, or $(C_{1-4})$alkoxy,
$R^2$ is a nitrogen-containing, basic substituent selected from the group consisting of amino, mono- or di-$(C_{1-4})$ alkylamino, aminomethyl, mono- or di-$(C_{1-4})$ alkyl-aminomethyl, amidino, guanidino and 2-imidazolino, said guanidino and 2-imidazolino being unsubstituted or substituted on a nitrogen atom thereof by $C_{1-4}$ alkyl, $C_{1-4}$ alkanoyl, benzoyl or benzoyl substituted by $C_{1-4}$ alkyl, $C_{1-4}$ alkoxy or amino,
$R^3$ is hydrogen, hydroxy, halogen, $(C_{1-4})$ alkyl, $(C_{1-4})$ alkoxy or a nitrogen-containing, basic substituent selected from the group consisting of amino, mono- or di-$(C_{1-4})$alkylamino, aminomethyl, mono- or di-$(C_{1-4})$ alkylaminomethyl, amidino, guanidino and 2-imidazolino, said guanidino and 2-imidazolino being unsubstituted or substituted on a nitrogen atom thereof by $C_{1-4}$ alkyl, $C_{1-4}$ alkanoyl, benzyl or benzoyl substituted by $C_{1-4}$ alkyl, $C_{1-4}$ alkoxy or amino, and $R^4$ is hydrogen or hydroxy; and a pharmaceutically or veterinarily acceptable carrier therefor.

9. The composition according to claim 8, wherein said compound is 3-amino- or 4-amino-2,6-dichlorophenylacetyl guanidine or 3-amino- or 4-amino-2,6-dichlorobenzylideneamine guanidine.

10. A method for treating diarrhoea and scours in human and non-human animals, which comprises administering an effective, non-toxic amount of a compound of formula (I) according to claim 1 to a human or non-human animal in need thereof.

11. A method for treating diarrhoea and scours in human and non-human animals, which comprises administering to a human or non-human animal in need thereof an effective, non-toxic amount of a compound of formula (I):

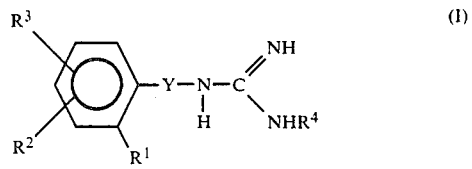

or a salt or acyl derivative thereof;

wherein
Y is either —CH=N— or

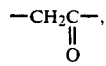

$R^1$ is hydroxy, halogen, ($C_{1-4}$) alkyl, or ($C_{1-4}$)alkoxy, $R^2$ is a nitrogen-containing, basic substituent selected from the group consisting of amino, mono- or di-($C_{1-4}$) alkylamino, aminomethyl, mono- or di-($C_{1-4}$) alkyl-aminomethyl, amidino, guanidino and 2-imidazolino, said guanidino and 2-imidazolino being unsubstituted or substituted on a nitrogen atom thereof by $C_{1-4}$ alkyl, $C_{1-4}$ alkanoyl, benzoyl or benzoyl substituted by $C_{1-4}$ alkyl, $C_{1-4}$ alkoxy or amino, $R^3$ is hydrogen, hydroxy, halogen, ($C_{1-4}$) alkyl, ($C_{1-4}$) alkoxy or a nitrogen-containing, basic substituent selected from the group consisting of amino, mono- or di-($C_{1-4}$)alkylamino, aminomethyl, mono- or di-($C_{1-4}$) alkylaminomethyl, amidino, guanidino and 2-imidazolino, said guanidino and 2-imidazolino being unsubstituted or substituted on a nitrogen atom thereof by $C_{1-4}$ alkyl, $C_{1-4}$ alkanoyl, benzoyl or benzoyl substituted by $C_{1-4}$ alkyl, $C_{1-4}$ alkoxy or amino, and $R^4$ is hydrogen or hydroxy.

12. The method according to claim 11, wherein $R^1$ and $R^3$ are halogen.

13. The method according to claim 11, which is 3-amino- or 4-amino-2,6-dichlorobenzylideneamino guanidine.

14. The method according to claim 11, wherein Y is —CH=N—.

15. The method according to claim 11, wherein said compound is 3-amino- or 4-amino-2,6-dichlorophenylacetyl guanidine or 3-amino- or 4-amino-2,6-dichlorobenzylideneamino guanidine.

* * * * *